United States Patent [19]
Tyle et al.

[11] Patent Number: 5,977,068
[45] Date of Patent: Nov. 2, 1999

[54] STABILIZED GROWTH HORMONE COMPOSITIONS

[75] Inventors: Praveen Tyle, Trenton; Brenda Lee Balint Probasco, New Egypt, both of N.J.; Susan Mancini Cady, Yardley, Pa.

[73] Assignee: American Cyanamid Company, Madison, N.J.

[21] Appl. No.: 07/808,694

[22] Filed: Dec. 16, 1991

Related U.S. Application Data

[63] Continuation of application No. 07/492,425, Mar. 6, 1990, abandoned, which is a continuation of application No. 06/920,537, Oct. 20, 1986, abandoned.

[51] Int. Cl.$^6$ .................................................. A61K 38/00
[52] U.S. Cl. ............................... 514/12; 514/2; 530/350; 530/324; 530/399; 930/120; 930/DIG. 800
[58] Field of Search .......................... 514/12, 2; 530/350, 530/324, 399; 930/120, DIG. 800

[56] References Cited

U.S. PATENT DOCUMENTS

| | | | |
|---|---|---|---|
| 4,248,634 | 2/1981 | Forester | 424/148 |
| 4,659,696 | 4/1987 | Hirai et al. | 514/16 |
| 4,670,419 | 6/1987 | Uda et al. | 514/16 |
| 4,719,111 | 1/1988 | Wilson | 514/925 |
| 4,917,685 | 4/1990 | Viswanathan et al. | 530/399 |

FOREIGN PATENT DOCUMENTS

| | | |
|---|---|---|
| 0085036 | 8/1983 | European Pat. Off. . |
| 2349738 | 4/1974 | Germany . |
| 736870 | 9/1955 | United Kingdom . |
| 1000897 | 8/1965 | United Kingdom . |
| 2104382 | 3/1983 | United Kingdom . |

OTHER PUBLICATIONS

Cenci et al., Chem. Abs. vol. 74, (1971), 98265r.
Papajova, Chem. Abs., vol. 81, (1974), 134682e.
Wasserman et al., Journal of Food Science, vol. 37, (1972), pp. 785–786.
The Condensed Chemical Dictionary, 9th Ed., p. 796.
Journal of Food Science, vol. 37, 1972, p. 785.

*Primary Examiner*—Ponnathapura Achutamurthy
*Assistant Examiner*—T. D. Wessendorf
*Attorney, Agent, or Firm*—Gregory M. Hill

[57] ABSTRACT

The present invention relates to compositions of growth hormones and preservatives which do not interfere with the activity of the growth hormone.

11 Claims, No Drawings

STABILIZED GROWTH HORMONE COMPOSITIONS

This is a continuation of application, Ser. No. 07/492,425, filed Mar. 6, 1990, which is a continuation application of Ser. No. 06/920,537, filed Oct. 20, 1986, both now abandoned.

BACKGROUND OF THE INVENTION

Recent developments in biotechnology have made biologically active macromolecules such as growth hormones available in large enough quantities to be considered for treating animals to obtain beneficial effects such as increased weight gains and increased milk production on a commercial scale.

Presently the administration of growth hormones to animals to obtain the above beneficial effects is accomplished by daily injection or periodic injection of compositions which deliver the hormone for extended periods of time such as those described in U.S. Pat. No. 4,452,775 teaching a cholesterol matrix delivery system for the sustained release of macro-molecules, including a variety of growth hormones. In actual practice and for convenience when hormone preparations are used, groups of animals are frequently injected with a stock preparation. It is therefore desirable to provide growth hormone compositions which contain antimicrobial preservatives such as antibacterial and antifungal agents to prevent mold, fungus and bacterial growth.

Unfortunately, due to the complex modes of action and intricate structures of biologically active macromolecules such as growth hormones many compounds which are normally used as preservatives interfere and/or interact with these hormones resulting in compositions which are either inactive or do not provide the expected level of biological response while other preservatives are not acceptable for use in animals which are used as a food source.

It is an object of this invention to provide growth hormone compositions containing preservatives which are suitable for use in animals to be used as a food source, retain the desired biological activity of the hormone and prevent the growth of fungus and/or bacteria.

SUMMARY OF THE INVENTION

The invention relates to compositions for parenteral administration to animals comprising a biologically active macromolecule of growth hormones, releasing factors, derivatives, analogs, or fragments thereof and a preservative of sorbic acid, dehydroacetic acid, or boric acid, or pharmaceutically or pharmacologically acceptable salts of these acids; salicylanilide; ethyl vanillin; sodium nitrate, sodium nitrite or mixtures thereof.

Surprisingly it has been found that in growth hormone compositions for parenteral administration to animals sorbic acid, dehydroacetic acid, or boric acid, or pharmaceutically or pharmacologically acceptable salts thereof; salicylanilide; ethyl vanillin; sodium nitrate, sodium nitrite or mixtures thereof can effectively prevent fungal and/or bacterial growth in the physiological pH range required for these compositions, and do not interfere with biological activity of the compositions.

Preferred compositions of this invention contain on a weight basis 0.002% to 0.2% of dehydroacetic acid, sorbic acid or boric acid or the sodium or potassium salts thereof; salicylanilide; ethyl vanillin; sodium nitrate, sodium nitrite or mixtures thereof; with the salts of dehydroacetic acid being most preferred.

It has been found in comparative testing of a wide variety of preservatives, that growth hormone compositions containing the preservatives of our invention, retain their activity across a wide pH range, including the physiological pH range, of about pH 7 to pH 10, the pH range in which these compositions are normally administered (i.e. pH7–pH10). Additionally, it has been found in comparative testing in hypophysectomized rats that compositions utilizing these preservatives retain their desired levels of biological activity.

The most preferred compositions of the invention employ dehydroacetic acid and salts thereof which have demonstrated retention of biological effectiveness, antibacterial activity and additionally pass microbiological preservative evaluation according to United States Pharmacopeia XXI.

Evaluation by hypophysectomized rat bioassay and microbiological preservative evaluations demonstrate that compositions of the invention containing sodium nitrate, sodium nitrite or mixtures thereof, boric acid, dehydroacetic acid or salts thereof and preferably sodium dehydroacetate show:

1. The concentration of viable bacteria are reduced to not more than 0.1% of the initial concentration by the fourteeth day, 2. The concentrations of viable yeasts and molds remain at or below the initial concentrations during the first 14 days, and 3. The concentration of each test microorganism remains at or below these designated levels during the remainder of the 28 day test period.

The invention is further illustrated by the following non limiting examples.

EXAMPLE 1

Biological Effectiveness of Bovine Growth Hormone Compositions Containing Preservatives Aqueous bovine growth hormone solutions in carbonate buffered saline ($Na_2CO_3$, 2.65 g/L; $NaHCO_3$, 2.10 g/L; NaCl, 8.50 g/L) containing the preservative listed in Table I below administered by subcutaneous injection to hypophysectomized albino rats (Taconic Farms, Sprague Dawley derived) for ten consecutive days at dosages of 80 and 10 mcg bSTH/rat/day. Bovine growth hormone produces increased growth in hypophysectomized rats, and the increased growth, as measured by total weight gain during the test period, is used to determine the biological efficacy of the aqueous compositions containing various preservatives.

The results of these experiments are summarized in Table I below which also indicates the type of approval each of the preservatives tested are listed as having in THE FOOD CHEMICAL NEWS GUIDE TO THE CURRENT STATUS OF FOOD ADDITIVES AND COLOR ADDITIVES. The type of approval is rated on a scale of 1 to 5 according to the rating system indicated below.

| Rating System | |
|---|---|
| Type of Approval | Approved for |
| 1 | (GRAS) Generally recognized as safe |
| 2 | Direct food additive |
| 3 | Indirect food additive |
| 4 | Food contact additive |
| 5 | Not approved |

TABLE I

Effectiveness of bovine growth hormone compositions containing preservatives

| Preservative | % w/v | Passed biological efficacy | Failed biological efficacy | Type of approval |
|---|---|---|---|---|
| Dehydroacetic acid | 0.1 | X | — | 2 |
| Sodium dehydroacetate | 0.1 | X | — | 2 |
| Sorbic acid | 0.1 | X | — | 1 |
| Potassium sorbate | 0.2 | X | — | 1 |
| Boric acid | 1.0 | X | — | 4 |
| Borax | 0.1 | X | — | 4 |
| Salicylanilide | 0.1 | X | — | 5 |
| o-vanillin | 0.1 | X | — | 5 |
| vanillin | 0.2 | — | X | 1 |
| ethyl vanillin | 0.1 | X | — | 1 |
| Sodium nitrate and Sodium nitrite | 0.16 0.04 | X | — | 2 |
| Sodium nitrite | 0.1 | X | — | 2 |
| Sodium o-phenylphenate | 0.1 | — | — | 3 |
| Thymol | 0.16 | — | X | 2 |
| Chlorhexidine | 0.4 | — | X | 5 |
| Thimerosal | 0.1 | — | X | 5 |
| Sodium thimerosal | 0.0025 | X | — | 5 |
| Chlorophenesin | 0.1 | X | — | 5 |
| Phenyl mercuric acetate | 0.005 | X | — | 5 |
| Phenyl mercuric acetate | 0.05 saturated solution | X | — | 5 |
| Methyl paraben | 0.3 | — | X | 2 |
| Methyl paraben | saturated solution | — | X | 2 |
| Butyl paraben | 0.3 | — | X | 2 |
| Chlorobutanol | 0.5 | — | X | 5 |
| Phenol | 0.2 | — | X | 4 |
| Phenol & glycerine | 0.2 | — | X | 4 |
| Phenyl mecuric acetate | 0.05 | X | — | 5 |
| Benzethonium chloride | 0.05 | — | X | 5 |
| Sodium azide | 0.2 | X | — | 5 |
| Nitrofurazone | 0.5 | X | — | 5 |

EXAMPLE 2

Microbiological Preservative Evaluation

Samples containing bovine growth hormone (900 mg), sodium carbonate (119.3 mg), sodium bicarbonate (283.5 mg) and preservatives at varying levels are dissolved in 90 mL of water. The solutions are lyophilized and gamma irradiated at 2.5 mrads at room temperature and are then reconstituted with irradiated normal saline (0.85% w/v NaCl) to give 10 mg/mL of hormone solution. The thus prepared samples are then subjected to microbiological preservative evaluation according to USP XXI as indicated by the testing procedure below.

Microbiological Preservative Evaluation According to USP XXI

1. Amount sample tested per culture: 20 grams or mL.

2. Temperature of incubation during test: 20–25° C.

3. Survivors enumerated by plate count at indicated intervals. Survivors recovered at 30–35° C. for fungi. Count=number of colony-forming units (CFU) per gram or per mL.

The results of these experiments which are summarized in Table II–IV below demonstrate the effectiveness of sorbic acid, dehydroacetic acids and salts of these acids, and salicylanilide for inhibiting fungal and/or bacterial growth in the compositions of the invention.

TABLE II

Dehydroacetic acid 0.1% w/v

| Organism | Inoculum | 7 Days | 14 Days | 21 Days | 28 Days |
|---|---|---|---|---|---|
| S. aureus | 185,000 | 63.5 | <1 | <1 | <1 |
| E. coli | 450,000 | <1 | <1 | <1 | <1 |
| Ps. aeruginosa | 105,500 | <1 | <1 | <1 | <1 |
| C. albicans | 156,000 | 10,850 | 4,550 | 1,470 | 1,130 |
| A. niger | 220,000 | 160,000 | 230,000 | 65,000 | 150,000 |

TABLE III

Sodium dehydroacetate 0.1% w/v

| Organism | Inoculum | 7 Days | 14 Days | 21 Days | 28 Days |
|---|---|---|---|---|---|
| S. aureus | 185,000 | 245 | <1 | <1 | <1 |
| E. coli | 450,000 | <1 | <1 | <1 | <1 |
| Ps. aeruginosa | 105,500 | <1 | <1 | <1 | <1 |
| C. albicans | 156,000 | 7,500 | 3,550 | 1,555 | 1,250 |
| A. niger | 220,000 | 220,000 | 215,000 | 115,000 | 190,000 |

TABLE IV

Sorbic acid 0.2% w/v

| Organism | Inoculum | 7 Days | 14 Days | 21 Days | 28 Days |
|---|---|---|---|---|---|
| S. aureus | 197,500 | 4500 | 80 | <1 | <1 |
| E. coli | 430,000 | 35 | 23.5 | <1 | <1 |
| Ps. aeruginosa | 185,500 | 35 | 18 | 17 | <1 |
| C. albicans | 520,000 | 5,500 | 100 | <1 | <1 |
| A. niger | 130,000 | 40,000 | 205,000 | 185,000 | 210,000 |

TABLE V

Potassium sorbate 0.2% w/v

| Organism | Inoculum | 7 Days | 14 Days | 21 Days | 28 Days |
|---|---|---|---|---|---|
| S. aureus | 197,500 | 1000 | 20 | <1 | <1 |
| E. coli | 430,000 | <10 | 3 | <1 | <1 |
| Ps. aeruginosa | 185,500 | 20 | <1 | 17 | <1 |
| C. albicans | 520,000 | 225,000 | 190,000 | 255,000 | 240,000 |
| A. niger | 130,000 | 150,000 | 225,000 | 130,000 | 85,000 |

TABLE VI

| | Salicylanilide 0.002% w/v | | | |
|---|---|---|---|---|
| Organism | Inoculum | 1 Day | 14 Days | 28 Days |
| S. aureus | 4,300,000 | 2,200,000 | <10 | <10 |
| E. coli | 3,000,000 | <10 | <10 | <10 |
| Ps. aeruginosa | 2,700,500 | <10 | <10 | <10 |
| C. albicans | 2,100,000 | 1,700,000 | 1,990,000 | 10 |
| A. niger | 470,000 | 550,000 | 540,000 | 480,000 |

What is claimed is:

1. A stable composition for parenteral administration to an animal consisting essentially of a biologically active macromolecule of a growth hormone, a releasing factor, a derivative, an analog or a fragment thereof and a preservative of sorbic acid, dehydroacetic acid, boric acid or a pharmaceutically acceptable salt thereof; salicylanilide; ethyl vanillin, sodium nitrate, sodium nitrite or a mixture thereof.

2. A composition according to claim 1 wherein the growth hormone is bovine growth hormone.

3. A composition according to claim 2 which includes on a weight to volume basis 0.002% to 0.2% of the preservative.

4. A composition according to claim 3 wherein the preservative is sodium nitrate, sodium nitrite or a mixture thereof.

5. A composition according to claim 4 wherein the preservative is sodium nitrite.

6. A composition according to claim 4 wherein the preservative is a mixture of sodium nitrate and sodium nitrite.

7. A composition according to claim 3 wherein the preservative is boric acid or borax.

8. A composition according to claim 7 wherein the preservative is borax.

9. A composition according to claim 3 wherein the preservative is dehydroacetic acid or a pharmaceutically acceptable salt thereof.

10. A composition according to claim 9 wherein the preservative is sodium dehydroacetate or potassium dehydroacetate.

11. A composition according to claim 1 wherein the growth hormone is porcine growth hormone.

* * * * *